US008419982B2

(12) United States Patent
Copp-Howland et al.

(10) Patent No.: US 8,419,982 B2
(45) Date of Patent: Apr. 16, 2013

(54) CONDUCTIVE COMPOSITIONS AND METHOD

(75) Inventors: Warren W. Copp-Howland, Chicopee, MA (US); David Selvitelli, Suffield, CT (US)

(73) Assignee: Covidien LP, Mansfield, MA (US)

( * ) Notice: Subject to any disclaimer, the term of this patent is extended or adjusted under 35 U.S.C. 154(b) by 353 days.

(21) Appl. No.: 12/208,424

(22) Filed: Sep. 11, 2008

(65) Prior Publication Data
US 2010/0059722 A1 Mar. 11, 2010

(51) Int. Cl.
*H01B 1/12* (2006.01)
(52) U.S. Cl.
USPC ...... 252/519.33; 600/372; 600/391; 600/395; 600/397; 607/2
(58) Field of Classification Search ............ 252/519.33; 600/371, 391, 372, 395, 397; 602/2
See application file for complete search history.

(56) References Cited

U.S. PATENT DOCUMENTS

| | | |
|---|---|---|
| 4,768,523 A | 9/1988 | Cahalan et al. |
| 4,911,855 A | 3/1990 | Rasicci et al. |
| 5,173,302 A | 12/1992 | Holmblad et al. |
| 5,234,992 A | 8/1993 | Gyory et al. |
| 5,338,490 A | 8/1994 | Dietz et al. |
| 5,674,275 A | 10/1997 | Tang et al. |
| 5,721,313 A | 2/1998 | Yueng et al. |
| 5,779,632 A * | 7/1998 | Dietz et al. ............ 600/391 |
| 5,985,990 A | 11/1999 | Kantner et al. |
| 6,038,464 A | 3/2000 | Axelgaard et al. |
| 6,263,226 B1 | 7/2001 | Axelgaard et al. |
| 6,447,798 B1 | 9/2002 | Munro et al. |
| 6,592,898 B2 | 7/2003 | Munro et al. |
| 6,613,030 B1 | 9/2003 | Coles et al. |
| 6,641,569 B1 | 11/2003 | Coles et al. |
| 6,683,120 B2 | 1/2004 | Munro et al. |
| 6,792,301 B2 | 9/2004 | Munro et al. |
| 6,887,917 B2 | 5/2005 | Yang et al. |
| 6,987,133 B2 | 1/2006 | Chen |
| 7,076,282 B2 | 7/2006 | Munro et al. |
| 2003/0232895 A1 | 12/2003 | Omidan et al. |
| 2005/0085706 A1* | 4/2005 | Perrault et al. ............ 600/391 |
| 2005/0136077 A1 | 6/2005 | Yahiaoui et al. |

(Continued)

FOREIGN PATENT DOCUMENTS

| | | |
|---|---|---|
| EP | 1 721 917 | 11/2006 |
| EP | 1 721 917 A1 | 11/2006 |

(Continued)

OTHER PUBLICATIONS

"Photoinitiators for Free-Radical Initiated Photoimaging Systems," by B.M. Monroe and G.C. Weed, Chem.Rev., 93, 435-448 (1993).

(Continued)

*Primary Examiner* — Mark Kopec
*Assistant Examiner* — Haidung Nguyen
(74) *Attorney, Agent, or Firm* — Lisa E. Winsor, Esq.

(57) ABSTRACT

Conductive compositions for use with medical electrodes are provided. The conductive compositions utilize a surfactant capable of both reducing the surface tension of the conductive composition as well as increasing the viscosity of the conductive composition. Methods of preparing these conductive compositions are also provided.

22 Claims, 1 Drawing Sheet

U.S. PATENT DOCUMENTS

| | | |
|---|---|---|
| 2005/0277991 A1 | 12/2005 | Covey et al. |
| 2007/0032719 A1 | 2/2007 | Menon et al. |
| 2007/0208130 A1* | 9/2007 | Sasahara et al. .............. 524/521 |
| 2007/0282188 A1 | 12/2007 | Copp-Howland |
| 2007/0282408 A1 | 12/2007 | Coggins |

FOREIGN PATENT DOCUMENTS

| | | |
|---|---|---|
| WO | WO 88/05666 A1 | 8/1988 |
| WO | WO 93/09713 | 5/1993 |
| WO | WO 03/051408 | 6/2003 |
| WO | WO 2007/063436 | 6/2007 |
| WO | WO 2007/083275 | 7/2007 |
| WO | WO 2007/142797 | 12/2007 |
| WO | WO 2007/142797 A2 | 12/2007 |

OTHER PUBLICATIONS

International Search Report from European Application No. EP 08 25 3592 dated Mar. 6, 2009.
Office Action issued in U.S. Appl. No. 11/442,797 mailed Jul. 23, 2009 (7 pages).
Office Action issued in U.S. Appl. No. 11/442,797 mailed Oct. 19, 2009 (5 pages).
Claims from co-pending U.S. Appl. No. 11/442,797 (10 pages).
European Search Report dated Jan. 15, 2010.
Search Report from corresponding European Application No. EP 10 16 0096 mailed Apr. 4, 2011.
The First Examination Report issued in the corresponding EP Application No. 09251989.1 mailed Nov. 27, 2012.

* cited by examiner

CONDUCTIVE COMPOSITIONS AND METHOD

TECHNICAL FIELD

The present disclosure relates to hydrophilic polymers and methods of making them. More particularly, the present disclosure relates to hydrophilic polymers suitable for use as conductive compositions, methods of making these compositions, and the use of these compositions with medical electrodes.

BACKGROUND OF RELATED ART

Medical electrodes are used to transmit electrical signals or currents between the body of a patient and external medical equipment. These electrodes typically include a conductive composition adhered to or otherwise in contact with, the skin of the patient, and a conductor, which is electrically connected to the conductive composition and to the external medical equipment.

Conventional conductive compositions include water containing hydrogels made from hydrophilic monomer solutions. Additives are commonly used to modify physical properties of conductive compositions resulting in compositions, such as hydrogels for use in medical electrodes, with uniform dimensions and performance properties. Polymeric thickeners have been used to increase the viscosity of monomer solutions, but may not prevent the solution from beading up on a hydrophobic surface (such as a film release liner) or lower the surface tension of the hydrophilic mixes. Polymeric thickeners usually require relatively high concentrations to achieve an effective viscosity and they tend to leave a residue after the monomer has been polymerized.

Surfactants have been used to lower the surface tension of the monomer mixes but they do not increase the viscosity. Moreover, even if the surfactant is added at relatively high levels, the monomer films are not dimensionally stable when coated on hydrophobic surfaces. Thus, conductive compositions for medical electrodes that are dimensionally stable on hydrophobic surfaces and that have uniform depth and performance properties may be desirable.

SUMMARY

A conductive composition is provided which includes from about 15 weight % to about 50 weight % of a humectant or a mixture of humectants; from about 18% to about 45% of a combination of monomers including, in polymerized form, from about 1 wt % to about 20 weight % of a first monomer, in which the first monomer includes a mixture of an organic acid selected from the group consisting of acrylic acid, methacrylic acid, itaconic acid, trans-cinnamic acid, crotonic acid, linoleic acid, linolenic acid, maleic acid, sorbic acid, and combinations thereof, one or more salts thereof, and from about 15 weight % to about 45 weight % of a second monomer, in which the second monomer is one or more monomers of the formula $CH_2=CHC(O)XR$, in which X is O or NH and R is an unsubstituted or substituted alkyl group of from about 1 to about 5 carbon atoms; from about 0.01% to about 0.5% of a surfactant capable of providing the composition with a viscosity of from about 250 cps to about 40,000 cps; and from about 0.05 weight % to about 7 weight % of a conditioning agent. A biomedical electrode including a substrate with a layer of the conductive composition as presently disclosed is also provided.

The surfactants of the present disclosure increase the viscosity of and lower the surface tension of the conductive composition. Suitable surfactants include octylphenol ethoxylates, nonylphenol ethoxylates, combinations thereof, and derivatives thereof.

A method for forming a conductive composition is also provided. Such a method may include, in embodiments, preparing a monomer reaction mixture including: from about 15 weight % to about 50 weight % of a humectant or a mixture of humectants; from about 18 weight % to about 45 weight % of a combination of monomers including from about 1 weight % to about 20 weight % of an organic acid selected from the group consisting of acrylic acid, methacrylic acid, itaconic acid, trans-cinnamic acid, crotonic acid, linoleic acid, linolenic acid, maleic acid, sorbic acid, one or more salts thereof, and combinations thereof, and from about 15 weight % to about 45 weight % of the sodium salt of 2-acrylamido-2-methylpropane sulfonic acid; from about 0.01 weight % to about 0.5 weight % of a surfactant; from about 0.05 weight % to about 7 weight % of a conditioning agent; and polymerizing the monomer or combination of monomers to form a copolymer as the conductive composition having a viscosity of from about 250 cps to about 40,000 cps.

DETAILED DESCRIPTION

Unless the context indicates otherwise, in the specification and claims, the terms first monomer, second monomer, humectant, electrolyte, polymerization initiator, polymerization inhibitor, crosslinking agent, neutralizer, salt, surfactant, conditioning agent, and similar terms also include mixtures of such materials. Unless otherwise specified, all percentages are percentages by weight and all temperatures are in degrees Centigrade (degrees Celsius).

Conductive Composition

The conductive composition, sometimes known as a hydrogel or a conductive hydrogel, is prepared by polymerizing a monomer reaction mixture including a humectant, an electrolyte, a first monomer, in which the first monomer may be a mixture of an organic acid such as acrylic acid, methacrylic acid, itaconic acid, trans-cinnamic acid, crotonic acid, linoleic acid, linolenic acid, maleic acid, sorbic acid, one or more salts thereof, and combinations thereof, and/or a salt thereof, and a second monomer, in which the second monomer may be one or more monomers of the formula $CH_2=CHC(O)XR$, in which X is O or NH and R is an unsubstituted or substituted alkyl group of from about 1 to about 5 carbon atoms; a surfactant; a conditioning agent; a polymerization initiator; a neutralizer such as sodium hydroxide; water; an optional crosslinking agent; and an optional polymerization inhibitor. The pH of the monomer reaction mixture, and of the resulting conductive composition, may be about 5 +/−0.2, in embodiments from about 2 to about 6, in other embodiments from about 2.6 to about 5. Medical electrodes including the conductive compositions of the present disclosure meet ANSI/AAMI standard EC 12:2000, both before and after storage at about 70° C. for about 120 days in sealed packaging, for example a sealed polyfoil pouch, to prevent loss of water from the compositions.

The conductive composition may include a humectant or a mixture of humectants. The humectant may be a non-volatile, non-toxic, water soluble or water miscible viscous liquid at room temperature. Suitable humectants include polyhydric alcohols such as glycerol, sorbitol, ethylene glycol, propylene glycol, polyethylene glycols such as PEG 400 and PEG 600, poly(propylene glycol), and mixtures thereof. In some embodiments, the humectant may include polyethylene glycol, sorbitol, glycerol, and mixtures thereof. In embodiments, the humectant may be present in an amount from about 15 weight % to about 50 weight % of the conductive composition, in other embodiments, from about 20 weight % to about 40 weight % of the conductive composition.

The conductive composition may also include an electrolyte or a mixture of electrolytes. The electrolyte may be a salt, such as lithium chloride, sodium chloride, potassium chloride, magnesium acetate, ammonium acetate, and/or mixtures thereof. In some embodiments, the electrolyte may include potassium chloride. In embodiments, the electrolyte may be present in an amount from about 0.1 weight % to about 8 weight % of the coating composition, in other embodiments, from about 1 weight % to about 4 weight % of the coating composition.

In embodiments, the conductive composition may include a monomer mix. The monomer mix may include a first monomer, a second monomer, and, optionally, a cross-linking agent. The first monomer may include an organic acid such as acrylic acid, methacrylic acid, itaconic acid, trans-cinnamic acid, crotonic acid, linoleic acid, maleic acid, sorbic acid, one or more salts thereof, and combinations thereof. Salts may include, for example, acrylates, methacrylates, itaconates, cinnamates, crotonates, linoleates, maleates, and sorbates. The polymer produced by polymerization thus may include acid acrylate moieties ($-CO_2H$ and/or $-CO_2M$, in which M is a cation such as sodium ion, potassium ion, lithium ion, ammonium or substituted ammonium ion, etc.) directly attached to the polymer backbone.

In embodiments, the second monomer may be one or more monomers of the formula $CH_2=CHC(O)XR$, in which X is O or NH, and R is an unsubstituted or substituted alkyl group of from about 1 to about 5 carbon atoms. The polymer produced by polymerization thus may include comprises groups of the structure $-CHC(O)XR$ directly attached to the polymer backbone.

Suitable unsubstituted alkyl groups include methyl, ethyl, n-propyl, n-butyl, and n-pentyl. Suitable substituents that may be present in a substituted alkyl group include halo (such as F, Cl, or Br), cyano, carboxylic acid and salts thereof (i.e., $-CO_2H$ or $-CO_2M$, in which M is a cation), phosphate and salts thereof, and sulfonic acid and salts thereof. An example of such a substituted alkyl group is (3-sulfopropyl)acrylic acid ester, potassium salt. In embodiments, the second monomer may include a 2-acrylamido-2-methylpropane sulfonic acid (AMPS) ($CH_2=CH-CONHC(CH_3)_2-CH_2-SO_3H$) and/or a salt thereof. Exemplary salts include sodium, lithium, potassium, ammonium, and substituted ammonium salts, and combinations thereof.

In embodiments, the monomer mix may be present in an amount from about 18 weight % to about 45 weight % of the reaction mixture, in embodiments, from about 20 weight % to about 40 weight % of the of the reaction mixture. Following the polymerization reaction, the conductive composition may include from about 18 weight % to about 45 weight % of the resulting monomer mix or monomer combination, in embodiments a polymer, in other embodiments, from about 20 weight % to about 40 weight % of the polymer. In the calculation of the percentage composition, acrylic acid and acrylic acid salt or salts are calculated as acrylic acid, and when 2-acrylamido-2-methylpropane sulfonic acid and/or a salt or salts thereof are present, they are calculated as the sodium salt of 2-acrylamido-2-methylpropane sulfonic acid (NaAMPS).

In embodiments, the first monomer may be present in an amount from about 1 weight % to about 20 weight % in the monomer mix, in other embodiments, from about 5 weight % to about 10 weight % in the monomer mix. In embodiments, the second monomer may be present in an amount from about 15 weight % to about 45 weight % in the monomer mix, in other embodiments from about 20 weight % to about 30 weight % in the monomer mix. In one embodiment, the acrylic acid and/or salt or salts thereof make up about 3 weight % of the monomer mix and the second monomer, such as 2-acrylamido-2-methylpropane sulfonic acid and/or salt or salts thereof, may make up about 30 weight % of the monomer mix.

In embodiments, the second monomer may be NaAMPS ($CH_2=CH-CONHC(CH_3)_2-CH_2-SO_3^-M^+$). In embodiments, the first monomer (acrylic acid and/or salt or salt thereof, calculated as acrylic acid) may be present in an amount from about 1 weight % to about 20 weight %, in other embodiments, from about 5 weight % to about 10 weight %, of the total amount. In embodiments, the NaAMPS (calculated as NaAMPS) may be present in an amount from about 15 weight % to about 45 weight %, in other embodiments, from about 20 weight % to about 30 weight %, of the total amount. In one embodiment, the first monomer may be present in an amount about 3 weight % to about 5 weight % of the monomer mix and the NaAMPS may be present in an amount from about 22 weight % to about 28 weight % of the total amount.

In accordance with the present disclosure, the conductive composition includes a surfactant which accomplishes both a thickening or an increase in the viscosity of the conductive composition while at the same time reducing the surface tension of the conductive composition. The viscosity generated is very pseudoplastic, which allows efficient coating of the conductive composition via a variety of coater types within the purview of those skilled in the art. The reduction of surface tension due to the surfactant also allows the coating composition to be coated as a thin layered film. At the same time, the increase in viscosity permits application of the conductive composition onto a hydrophobic film without the need for an additional support material such as a scrim or similar component.

In embodiments, the surfactant may include octylphenol ethoxylates, nonylphenol ethoxylates, derivatives thereof, and combinations thereof. Suitable octylphenol ethoxylates include octoxynol-7 and octoxynol-9. Octoxynol-7, also known as TRITON® X114, is commercially available from DOW Chemical Corporation. Octoxynol-9, also known as TRITON® X100, is commercially available from DOW Chemical Corporation. Suitable nonylphenol ethoxylates include nonoxynol-7 and nonoxynol-9. Nonoxynol-7, also known as TERGITOL® NP-7, is commercially available from DOW Chemical Corporation. Nonoxynol-9, also known as TERGITOL® NP-9, is commercially available from DOW Chemical Corporation.

The surfactant capable of thickening and surface tension reduction may be present in conductive compositions of the present disclosure in low amounts. In embodiments, the conductive composition may include the above surfactants in an amount from about 0.01 weight % to about 0.5 weight %, in other embodiments from about 0.06 weight % to about 0.2 weight %, in still other embodiments from about 0.08 weight % to about 0.15 weight %.

The conductive composition may also include a conditioning agent. Suitable conditioning agents include silica, powdered carbon, kaolin clay, powdered cellulose, combinations thereof, and the like. The conditioning agent may be present in an amount from about 0.05 weight % to about 7 weight % of the conductive composition, in embodiments from about 1 weight % to about 6 weight % of the conductive composition. Without wishing to be bound by any theory, the silica may be important in generating the increased viscosity observed with the surfactants described above.

Optionally, the monomer reaction mixture may include an effective amount, in embodiments about 0.1 weight % or less of a cross-linking agent or mixture of cross-linking agents. An effective amount of cross-linking agent is an amount that produces a conductive composition with the desired physical properties, such as coherence and adhesion, and electrical properties.

Suitable crosslinking agents include free radical polymerizable monomers that include more than one ethylenically unsaturated, free radical polymerizable group. The effective amount of crosslinking agent may be soluble in the mixture. Numerous crosslinking agents polymerizable by free-radical initiated polymerization are within the purview of those skilled in the art. Crosslinking agents include, for example, bis-acrylamides and methacrylamides, such as N,N'-methylene bis-acrylamide; acrylate and methacrylate esters of polyols, such as, ethylene glycol diacrylate and dimethacrylate, diethylene glycol diacrylate and dimethacrylate, trimethylolpropane triacrylate and trimethacrylate, ethoxylated trimethylolpropane triacrylate and trimethacrylate; pentaerythritol triacrylate and trimethacrylate, pentaerythritol tetraacrylate and tetramethacrylate, polyethylene glycol diacrylates and dimethacrylates, such as the diacrylates and dimethacrylates of polyethylene glycols having a molecular weight of from about 200 to about 600, combinations thereof, and the like. In embodiments, the crosslinking agent may include N,N'-methylene bis-acrylamide [$(CH_2=CHCONH)_2CH_2$].

The crosslinking-agent may be added to the monomer reaction mixture to speed up processing, as, for example, a 1% solution in deionized water. The amount of crosslinking agent is calculated as the amount of the crosslinking agent added, not as the amount of solution containing crosslinking agent added. The water in which the crosslinking agent is dissolved is counted as part of the water present in the mixture.

Although the amount required will depend on, for example, the molecular weight of the cross-linking agent, the number of ethylenically unsaturated, free radical polymerizable groups present in the cross-linking agent, the amount of free radical polymerizable monomers present in the monomer mix, and the like, when the cross-linking agent is present, the amount of crosslinking agent may be from about 0.01 weight % to about 0.08 weight % of the total weight of the monomer mix, in embodiments from about 0.02 weight % to about 0.05 weight % of the total weight of the monomer mix, calculated as described above.

The monomer reaction mixture may also include an effective amount of a polymerization initiator. An effective amount is an amount that produces efficient polymerization of the monomers under the polymerization conditions to produce a conductive composition with the desired physical and chemical properties. Numerous free radical polymerization initiators are within the purview of those skilled in the art. The polymerization initiator may be a single compound or a mixture of compounds. Thermal and/or photo free radical polymerization initiators, for example, may be used. Suitable thermal free radical polymerization initiators include azo compounds, such as 2,2-azobisisobutyronitrile (AIBN). Suitable photo free radical polymerization initiators include those disclosed in "Photoinitiators for Free-Radical-Initiated Photoimaging Systems," by B. M. Monroe and G. C. Weed, *Chem. Rev.*, 93, 435-448 (1993) and in "Free Radical Polymerization" by K. K. Dietliker, in *Chemistry and Technology of UV and EB Formulation for Coatings, Inks, and Paints*, P. K. T. Oldring, ed., SITA Technology Ltd., London, 1991, Vol. 3, pp. 59-525.

Polymerization initiators may also include those which generate radicals by photolysis, for example, benzoin derivatives, benzophenone, acyl phosphine oxides, photoredox systems, and the like, and combinations thereof. Suitable initiators generating radicals as a result of a redox reaction may include of a combination of an oxidant and a reducing agent. Suitable oxidants may include potassium peroxydisulfate, hydrogen peroxide, tert-butyl hydroperoxide, cumyl hydroperoxide, benzoyl peroxide, p-menthane hydroperoxide, and the like, and combinations thereof. Suitable reducing agents may include Fe(II) salts, i.e. ferrous sulfates including ferrous sulfate heptahydrate, Ti(III) salts, potassium thiosulfate, potassium bisulfite, potassium persulfate, potassium disulfite, ascorbic acid and its salts, oxalic acid and salts thereof, hydrogen peroxide, dextrose, and the like, and combinations thereof.

In embodiments, free radical photo polymerization initiators may include, for example, 1-hydroxycyclohexylphenyl ketone (HCPK, IRGACURE® 184); 2-hydroxy-2-methyl-1-phenylpropan-1-one (DAROCUR® 1173); 2-hydroxy-1-[4-(2-hydroxyethoxy)phenyl]-2-methyl-1-propan-1-one (IRGACURE®2959), 2,2-dimethoxy-2-phenylacetophenone (benzildimethyl ketal, BDK, IRGACURE®651), a mixture of 50 weight % benzophenone and 50 weight % of 1-hydroxycyclohexylphenyl ketone (IRGACURE® 500), combinations thereof, and the like. In embodiments, the monomer reaction mixture may include the polymerization initiator in an amount from about 0.05 weight % to about 1 weight % of the monomer reaction mixture, in other embodiments, from about 0.2 weight % to about 0.6 weight % of the monomer reaction mixture. In embodiments, about 3% polymerization inhibitor may be added to a 2-propanol solution to aid in solubility.

The monomer reaction mixture may also include a neutralizer. Bases such as hydroxides, amines, Lewis bases, and mixtures thereof may be used as neutralizers. The neutralizer may be a base such as ammonium hydroxide, sodium hydroxide, potassium hydroxide, lithium hydroxide, combinations thereof, and the like. If the organic acid and/or the second monomer, such as the 2-acrylamido-2-methylpropane sulfonic acid, are added to the mixture at least partly in the acid form, it may be necessary to add neutralizer to the mixture to neutralize some of the acid so that the pH of the mixture is from about 3 to about 6. In one embodiment, all the 2-acrylamido-2-methylpropane sulfonic acid in the monomer reaction mixture is neutralized (i.e., present as a salt rather than as the acid), so 2-acrylamido-2-methylpropane sulfonic acid may be added to the monomer reaction mixture and neutralized by addition of a neutralizer.

Alternatively, a salt or salts of the second monomer, such as the sodium salt, may be added so that the addition of a neutralizer to convert the acid form of the second monomer to a salt is unnecessary. In some embodiments, only part of the acid, for example, acrylic acid, is neutralized (i.e., present as a salt). Consequently, if acrylic acid is added, a neutralizer may be necessary to convert part of the acrylic acid to a salt or a mixture of salts.

Alternatively, an appropriate mixture of acrylic acid and a salt or a mixture of salts may be added so addition of a neutralizer to convert part of the acrylic acid to a salt or mixture of salts is unnecessary. In embodiments, from about 10 mol % to about 60 mol % of the acrylic acid, in other embodiments from about 25 mol % to about 50 mol % of the acrylic acid, maybe present in the monomer reaction mixture as a salt.

When acrylic acid and NaAMPS are present in the monomer reaction mixture, a neutralizer, in embodiments sodium hydroxide, may be added. The amount of neutralizer added may be less than the amount necessary to neutralize all the acrylic acid in the mixture, so that the resulting mixture has a pH of from about 3 to about 6. In embodiments, from about 10 mol % to about 60 mol % of the acrylic acid, in other embodiments from about 25 mol % to about 50 mol % of the acrylic acid, may be neutralized by the neutralizer.

When sodium hydroxide is used as the neutralizer, in embodiments, from about 0.1 weight % to about 3.5 weight % sodium hydroxide (dry weight) may be added to the mixture. The sodium hydroxide may be conveniently added to the mixture as a water solution, such as, for example, an aqueous 50 weight % sodium hydroxide solution.

Water may be present in the mixture. The amount of water includes any water present in any of the ingredients and any water added with ingredients that are in water solution, such as the monomers, the crosslinking agent, the neutralizer, the humectant, and the like.

As will be apparent to those skilled in the art, when neutralizer is added to neutralize the organic acid and/or the second monomer, water will be generated by the neutralization reaction. When the water produced by the neutralization reaction, if any, is included, the mixture may thus possess from about 6 weight % to about 40 weight % water. When the water produced by partial neutralization of the acid is not included, the mixture may possess from about 5 weight % to about 35 weight % water.

In addition to the free radical initiator, small amounts of free radical polymerization inhibitors may be present in one or more of the monomers, and/or the crosslinking agent, and/or may be added to the mixture to prevent premature polymerization of the reaction mixture. In embodiments, free radical polymerization inhibitors may include, for example, hydroquinone, 4-methoxyphenol, di-t-butyl-p-cresol, pyrogallol, t-butyl catechol, benzoquinone, 4,4'-thio-bis-(3-methyl-6-t-butylphenol), and 2,2'-methylene-bis-(4-methyl-6-t-butylphenol). When present, the amount of the polymerization inhibitor may be from about 0.01 weight % to about 5 weight % of the mixture. Other conventional ingredients of conductive compositions may be present in the monomer reaction mixture or added to the conductive composition following the polymerization reaction.

The monomer reaction mixture of the above components may be applied to any suitable substrate, including any layer or component of an electrode. The monomer reaction mixture may be applied on a release liner, for example, a siliconized release substrate such as silicone coated polyethylene terephthalate film, or other substrate, prior to polymerization. Free radical polymerization may be initiated by, for example, heating the mixture when a thermal free radical polymerization initiator is present in the mixture, or exposing the mixture to actinic radiation when a photoinitiated free radical polymerization initiator is present in the mixture.

Free-radical polymerization may also be initiated by, for example, in an aqueous polymerization medium in the presence of a redox system including an oxidizing agent and a chelatable metal reducing agent having a reduced and oxidized form. As the oxidizing agent, a persulfate such as ammonium, sodium, or potassium persulfate or hydrogen peroxide may be used. As the chelatable metal reducing agent, a salt such as ferrous sulfate or a double salt such as ferrous ammonium sulfate may be used. Other similar oxidizing components as well as other chelatable metal reducing agents of the type described may also be used.

As noted above, the use of the surfactants described above provides the conductive composition with reduced surface tension which permits application of the conductive composition as a thin layered film, while at the same time the conductive composition possesses a viscosity that permits application without additional support layers such as scrims, reinforcing films, and the like.

For photoinitiation, any convenient source or sources of actinic radiation providing wavelengths in the region of the spectrum that overlap the absorption bands of the photoinitiated free radical polymerization initiator can be used to activate polymerization. The radiation can be natural or artificial, monochromatic or polychromatic, incoherent or coherent, and for high efficiency should correspond closely in wavelengths to the absorption bands of the polymerization initiator. Conventional light sources include fluorescent lamps, mercury vapor lamps, metal additive lamps, and arc lamps. Useful lasers include those whose emissions fall within or overlap the absorption bands of the photoinitiated free radical polymerization initiator.

Although the mixture may be degassed before polymerization and/or the polymerization may be carried out under an inert atmosphere, it is not necessary to degas the mixture before polymerization or to carry out the polymerization under an inert atmosphere.

Following polymerization, the resulting conductive composition may be transferred to a conductive substrate. Alternatively, the conductive composition may be adhered to a conductive substrate, and the release liner left in place to protect the conductive composition until it is ready for use.

The viscosity of conductive compositions of the present disclosure may vary depending on the components utilized to form the conductive composition, including the surfactant utilized and conditioning agent, if any. Suitable viscosities may be from about 50 cps to about 40,000 cps, in embodiments from about 250 cps to about 40,000 cps.

In embodiments where an octylphenol ethoxylate is utilized as a surfactant, the conductive compositions may have a viscosity of from about 250 cps to about 1500 cps, in embodiments from about 300 cps to about 1500 cps. For example, where octoxynol-7 is utilized as a surfactant, the conductive composition of the present disclosure may have a viscosity of from about 250 cps to about 400 cps, in embodiments from about 300 cps to about 400 cps. Where octoxynol-9 is utilized as a surfactant, the conductive composition of the present disclosure may have a viscosity of from about 400 cps to about 1100 cps, in embodiments from about 550 cps to about 1100 cps.

Where nonylphenol ethoxylates are utilized as the surfactants, the conductive composition may have a viscosity of from about 500 cps to about 40,000 cps, in embodiments from about 1000 cps to about 25,000 cps. For example, where nonoxynol-7 is utilized as a surfactant, the conductive composition of the present disclosure may have a viscosity of from about 1500 cps to about 4800 cps, in embodiments from about 1500 cps to about 3100 cps. Where nonoxynol-9 is utilized as a surfactant, the conductive composition of the present disclosure may have a viscosity of from about 1200 cps to about 40,000 cps, in embodiments from about 2100 cps to about 40,000 cps.

The conductive compositions of the present disclosure may be especially useful in medical electrodes that can be used with medical equipment for a variety applications, such as: electrocardiogram monitoring (ECG) electrodes (tab and snap style) for monitoring heart activity and for diagnosing heart abnormalities; electroencephalogram (EEG) electrodes; transcutaneous electrical nerve stimulation (TENS) electrodes used for pain management; neuromuscular stimulation (NMS) used for treating conditions such as scoliosis; muscle stimulation electrodes; wound treatment electrodes (accelerated healing of skin wounds or broken bones); defibrillation electrodes to dispense electrical energy to a chest cavity of a mammalian patient to defibrillate heart beats of the patient; and dispersive electrodes to receive electrical energy dispensed into an incision made during electrosurgery. Other applications of the conductive compositions of the present disclosure include, for example, electro-surgical dispersive pads; drug delivery (passive or iontophoretic); pre-surgical limb or area markers; tapes (anchoring chest tubes, NG tubes, IVs, cannulae, etc); and sterile seals at needle or cannula entry points. Medical equipment used in these applications is within the purview of those skilled in the art.

Medical Electrodes

Medical electrodes transmit electrical signals or currents to or from a patient's skin and an external medical apparatus. Medical electrodes are within the purview of those skilled in the art. These electrodes include a conductive composition on a substrate. The layer of conductive composition is in contact with the skin of the patient. The medical electrode may also include a conductive interface that is electrically connected to the layer of conductive composition and adapted to be electrically connected to an item of external medical equipment. For many applications, the conductive composition must also be sufficiently adhesive to adhere to the patient's skin. The configuration of the electrode and the adhesive properties required will depend on the intended application, such as whether the electrode is a transmission electrode, i.e., an electrode that sends electric currents or signals to the patient's body, or a sensing or monitoring electrode, i.e., an electrode that sends electrical signals from the patient's body to the external medical equipment.

Figure 1:
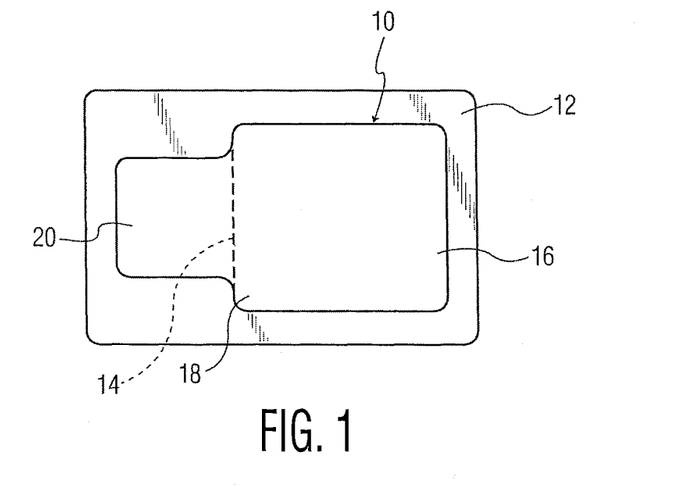
FIG. 1 is a top plan view of a medical electrode including the conductive composition of the present disclosure.
Figure 2:
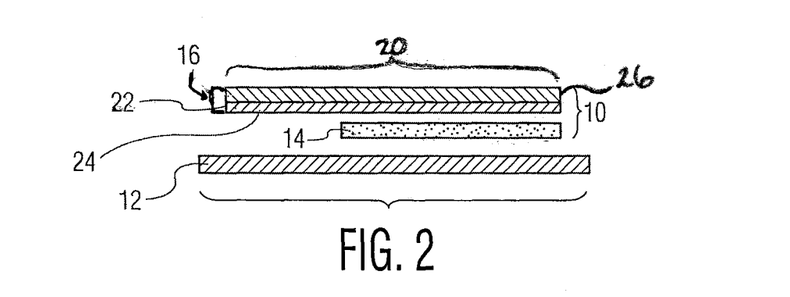
FIG. 2 is a cross-sectional view of the medical electrode of FIG. 1.

FIG. 1 and FIG. 2 show a medical electrode 10 on release liner 12. Release liner 12 is a release paper or film of a waxed or coated plastic, such as a silicone coated polyethylene terephthalate film, which may be used to protect medical electrode 10 before application of the electrode to a skin surface.

More specifically, as illustrated in FIGS. 1 and 2, electrode 10 has a release liner 12 attached and includes a conductive composition or hydrogel 14 thereon. Electrode 10 also includes a conductive member or interface 16, a portion 20 of which extends beyond conductive composition 14 for mechanical and electrical contact with the external medical equipment and to provide a conductive path. Conductive interface 16 includes conductive layer 24 which is in contact with conductive composition 14. Conductive interface 16 may also include a nonconductive layer 26 in contact with conductive layer 24 on side 22 of nonconductive layer 26. In use, release liner 12 is removed. Electrode 10 is applied to the surface of the patient's skin and electrically connected to the external medical equipment (not shown) by any connection means well known in the art. Electrode 10 may, by way of example, be connected to an electrocardiogram monitoring machine (ECG) by means of an "alligator" style clip and attached to portion 20.

Figure 3:
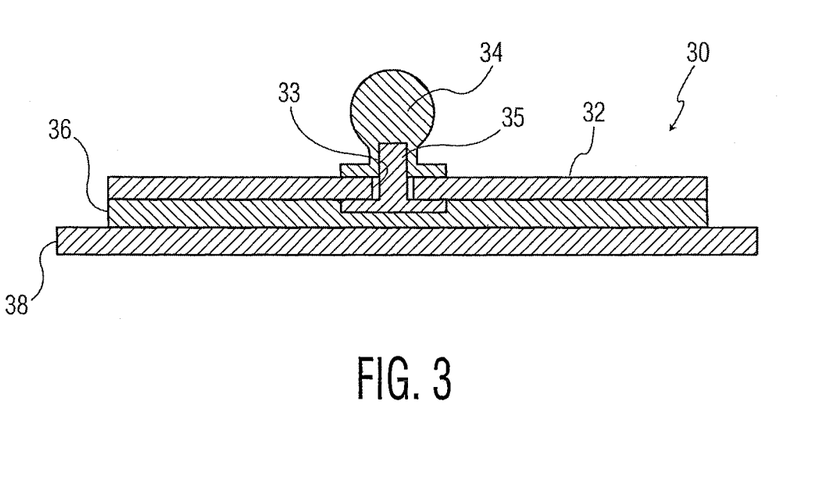
FIG. 3 is a cross-sectional view of a snap medical electrode.

FIG. 3 shows a cross-section of snap medical electrode 30 on a release liner 38. Electrode 30 has nonconductive backing 32, which has opening 33 covered by snap 34 through which eyelet 35 protrudes. Snap 34 is secured to eyelet 35. Together snap 34 and eyelet 35 include at least part of a conductive pathway to provide an electrical connection between conductive composition 36 and the external medical equipment (not shown). Release liner 38 protects the conductive composition 36 prior to use.

The conductive compositions of the present disclosure and medical electrodes including these compositions meet ANSI/AAMI standard EC 12:2000 for medical electrodes both before and after storage at 70° C. for 120 days with appropriate packaging to prevent loss of water from the composition, which is equivalent to storage at 20° C. for about 10 years with appropriate packaging to prevent loss of water.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLES 1-9

Preparation of the conductive compositions. Conductive compositions of the present disclosure were prepared with the components identified in Tables 1A, 1B, and 1C below. Briefly, the components listed in Tables 1A, 1B, and 1C were mixed together to form the monomer reaction mixtures. The ingredients were added in the following order: second monomer NaAMPS solution, crosslinking agent (1% N,N-methylene bis-acrylamide (MBA) solution), first monomer acrylic acid solution, electrolyte (potassium chloride), humectant (glycerol), conditioning agent (silica), neutralizer (sodium hydroxide), catalyst (polymerization initiator IRGACURE® 184), and surfactant. The mix time depended on the volume. When all components were completely dissolved and/or the mixture was homogenous, the monomer reaction mixture was coated onto a hydrophobic substrate, for example, siliconized release liner or film, without scrim. The layer of the mixture had a thickness of from about 0.01 to 0.25 inches. The monomer reaction mixture can also be injected into a retaining ring or molded directly and polymerized.

Specifically, the conductive composition was prepared as follows. The second monomer NaAMPS solution was weighed out into a clean 600 ml glass beaker. The beaker was placed under an electric mixer equipped with a three blade propeller style mixing rod. The cross-linking agent was weighed out and poured into the mixing vortex of the monomer solution. The acrylic acid was weighed out and added to the mixing vortex of the second monomer solution. The water was weighed out and added to the mixing vortex of the monomer solution. The salt was weighed out and added to the mixing vortex of the monomer solution. Mixing continued for 10 minutes to insure complete dissolution of the salt.

The glycerol was weighed out and added to the mixing vortex of the monomer solution. The silica was weighed out and added to the mixing vortex of the monomer solution. A calibrated pH probe was placed on the edge of the mixing vortex. The sodium hydroxide was added drop wise to bring the pH of the solution up to about 5±0.05. There was a slight temperature increase due to the heat of neutralization. However, care was taken to keep the temperature of the neutralized monomer solution under 40° C. (If the temperature were allowed to go above 40° C., there would be a significant risk of auto-polymerization.) The pH probe was then removed and cleaned.

The catalyst was weighed out and added to the mixing vortex of the monomer solution. Mixing was continued for one half hour to insure complete dissolution of the catalyst and a homogeneous solution was created. The surfactant was then added to the mixing vortex of the monomer solution and mixed for two minutes.

Air entrainment at this stage was minimized by slowing the mixer speed. The solution was coated at 0.025 inches thick on a 0.0065 inch polyethylene terephthalate (PET) release liner. The solution was irradiated 25 seconds under a xenon arc UV lamp. The resulting polymer film was covered with a 0.003 inch release coated polyethylene film.

Details of each of the monomer solutions and resulting films of Examples 1-9 are set forth in Tables 1A, 1B and 1C below.

TABLE 1A

| | Examples | | | | | | | | |
|---|---|---|---|---|---|---|---|---|---|
| | 1 | 2 | 3 | 4 | 5 | 6 | 7 | 8 | 9 |
| 58% NaAMPS | 116 | 145 | 145 | 116 | 145 | 116 | 116 | 145 | 130.5 |
| Acrylic acid | 30 | 30 | 30 | 30 | 30 | 30 | 30 | 30 | 30 |
| 1% MBA | .15 | .225 | .15 | .225 | .15 | .225 | .15 | .225 | .1875 |
| Water | 0 | 0 | 50 | 50 | 0 | 0 | 50 | 50 | 25 |
| KCl | 10 | 10 | 10 | 10 | 10 | 10 | 10 | 10 | 10 |
| Glycerol | 226 | 168.5 | 126 | 168.5 | 154.5 | 197 | 154.5 | 97 | 155.75 |
| Silica | 12.5 | 12.5 | 12.5 | 12.5 | 12.5 | 12.5 | 12.5 | 12.5 | 12.5 |
| Target pH | 3.5 | 3.5 | 3.5 | 3.5 | 5 | 5 | 5 | 5 | 4.25 |
| NaOH added | 1.14 | 1.16 | 1.52 | 1.78 | 18.14 | 18.84 | 21.22 | 21.86 | 4.88 |
| 3% Irgacure | 2.5 | 2.5 | 2.5 | 2.5 | 2.5 | 2.5 | 2.5 | 2.5 | 2.5 |
| Nonoxynol-9 | 0.5 | 0.5 | 0.5 | 0.5 | 0.5 | 0.5 | 0.5 | 0.5 | 0.5 |
| Total | 497.64 | 497.66 | 498.02 | 498.28 | 493.40 | 493.84 | 496.22 | 496.86 | 484.88 |
| Initial pH | 2.59 | 2.69 | 2.62 | 2.54 | 2.68 | 2.57 | 2.53 | 2.67 | 2.6 |
| After NaOH | 3.5 | 3.5 | 3.5 | 3.5 | 5 | 5 | 5 | 5 | 4.25 |
| Temp | 21 | 21 | 21 | 20 | 29 | 30 | 30 | 29.5 | 25 |
| Target Coating Width | 1.8 | 1.8 | 1.8 | 1.8 | 1.8 | 1.8 | 1.8 | 1.8 | 1.8 |
| Actual Width | 0.99 | 1.16 | 1.84 | 1.86 | 1.86 | 1.78 | 1.81 | 1.82 | 1.87 |
| Width Loss % | 45 | 36 | −2 | −3 | −3 | 1 | −1 | −1 | −4 |

TABLE 1B

| | Examples | | | | | | | | |
|---|---|---|---|---|---|---|---|---|---|
| | 1 | 2 | 3 | 4 | 5 | 6 | 7 | 8 | 9 |
| 58% NaAMPS | 200 | 250 | 250 | 200 | 250 | 200 | 200 | 250 | 225 |
| Acrylic acid | 30 | 30 | 30 | 30 | 30 | 30 | 30 | 30 | 30 |
| 1% MBA | .15 | .225 | .15 | .225 | .15 | .225 | .15 | .225 | .1875 |
| Water | 0 | 0 | 50 | 50 | 0 | 0 | 50 | 50 | 25 |
| KCl | 10 | 10 | 10 | 10 | 10 | 10 | 10 | 10 | 10 |
| Glycerol | 226 | 168.5 | 126 | 168.5 | 154.5 | 197 | 154.5 | 97 | 155.75 |
| Silica | 12.5 | 12.5 | 12.5 | 12.5 | 12.5 | 12.5 | 12.5 | 12.5 | 12.5 |
| Target pH | 3.5 | 3.5 | 3.5 | 3.5 | 5 | 5 | 5 | 5 | 4.25 |
| NaOH added | 3.60 | 3.50 | 3.50 | 3.50 | 25.00 | 25.00 | 25.00 | 25.00 | 25.00 |
| 3% Irgacure | 2.5 | 2.5 | 2.5 | 2.5 | 2.5 | 2.5 | 2.5 | 2.5 | 2.5 |
| Nonoxynol-9 | 0.5 | 0.5 | 0.5 | 0.5 | 0.5 | 0.5 | 0.5 | 0.5 | 0.5 |
| Total | 496.50 | 496.50 | 496.50 | 496.50 | 475.00 | 475.00 | 475.00 | 475.00 | 480.00 |

TABLE 1C

| | Examples | | | | | | | | |
|---|---|---|---|---|---|---|---|---|---|
| | 1 | 2 | 3 | 4 | 5 | 6 | 7 | 8 | 9 |
| 58% NaAMPS | 40 | 50 | 50 | 40 | 50 | 40 | 40 | 50 | 45 |
| Acrylic acid | 6 | 6 | 6 | 6 | 6 | 6 | 6 | 6 | 6 |
| 1% MBA | .03 | .045 | .03 | .045 | .03 | .045 | .03 | .045 | .0375 |
| Water | 0 | 0 | 10 | 10 | 0 | 0 | 10 | 10 | 5 |
| KCl | 2 | 2 | 2 | 2 | 2 | 2 | 2 | 2 | 2 |
| Glycerol | 45.20 | 33.70 | 25.20 | 33.70 | 30.90 | 39.40 | 30.90 | 19.40 | 31.15 |
| Silica | 2.5 | 2.5 | 2.5 | 2.5 | 2.5 | 2.5 | 2.5 | 2.5 | 2.5 |
| Target pH | 3.5 | 3.5 | 3.5 | 3.5 | 5 | 5 | 5 | 5 | 4.25 |
| NaOH added | 3.60 | 3.50 | 3.50 | 3.50 | 25.00 | 25.00 | 25.00 | 25.00 | 25.00 |
| 3% Irgacure | 0.5 | 0.5 | 0.5 | 0.5 | 0.5 | 0.5 | 0.5 | 0.5 | 0.5 |
| Nonoxynol-9 | 0.1 | 0.1 | 0.1 | 0.1 | 0.1 | 0.1 | 0.1 | 0.1 | 0.1 |
| Total | 99.30 | 99.30 | 99.30 | 99.30 | 95.00 | 95.00 | 95.00 | 95.00 | 96.00 |

The viscosity of each example, i.e., Examples 1-9, was measured with a viscometer commercially available from Brookfield Engineering Laboratories. All monomer solutions in Examples 1-9 were mixed with surfactant nonoxynol-9 and were measured at a temperature of 19.5° C. The viscosity was measured at speeds of 2, 4, 10, and 20 rpms in cps (centipoise) units. The viscosity of each of Examples 1-9 is summarized in Table 2 below.

TABLE 2

| Viscosity Spindle #3 | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| rpm 2 | 500 | 250 | 2250 | 4750 | 4000 | 9500 | 20750 | 20500 | 3250 |
| rpm 4 | 500 | 375 | 1250 | 2750 | 2625 | 5875 | 11625 | 11875 | 2000 |
| rpm 10 | 400 | 250 | 700 | 1400 | 1400 | 3100 | 5200 | 5250 | 1100 |
| rpm 20 | 375 | 225 | 450 | 875 | 950 | 2000 | 2875 | 1325 | 70 |

EXAMPLES 10-14

Surfactant Comparison. All monomer solutions were mixed as described above in Examples 1-9 with the appropriate surfactant indicated below and were measured at a temperature of 19° C. Example 10 was a control with no surfactant, Example 11 utilized octoxynol-7 as a surfactant, Example 12 utilized octoxynol-9 as a surfactant, Example 13 utilized nonoxynol-7 as a surfactant, and Example 14 utilized nonoxynol-9 as a surfactant. The results are set forth in Tables 3-7 below. The viscosity was measured with a viscometer commercially available from Brookfield Engineering Laboratories as described above in Examples 1-9.

TABLE 3

Example 10 (Control (no surfactant added))

| | Speed (rpm) | | | |
|---|---|---|---|---|
| | 2 | 4 | 10 | 20 |
| Dial Reading | 0.5 | 0.5 | 2 | 3.5 |
| Viscosity (cps) | 250 | 125 | 200 | 175 |

TABLE 4

Example 11 (Octoxynol-7)

| | Speed (rpm) | | | |
|---|---|---|---|---|
| | 2 | 4 | 10 | 20 |
| Dial Reading | 0.5 | 1.5 | 3.5 | 6 |
| Viscosity (cps) | 250 | 375 | 350 | 300 |

TABLE 5

Example 12 (Octoxynol-9)

| | Speed (rpm) | | | |
|---|---|---|---|---|
| | 2 | 4 | 10 | 20 |
| Dial Reading | 2 | 3.5 | 6 | 9.5 |
| Viscosity (cps) | 1000 | 875 | 600 | 475 |

TABLE 6

Example 13 (Nonoxynol-7)

| | Speed (rpm) | | | |
|---|---|---|---|---|
| | 2 | 4 | 10 | 20 |
| Dial Reading | 9.5 | 12 | 16 | 21 |
| Viscosity (cps) | 4750 | 3000 | 1600 | 1050 |

TABLE 7

Example 14 (Nonoxynol-9)

| | Speed (rpm) | | | |
|---|---|---|---|---|
| | 2 | 4 | 10 | 20 |
| Dial Reading | 13 | 16 | 21.5 | 28 |
| Viscosity (cps) | 6500 | 4000 | 2150 | 1400 |

As can be seen from Tables 3-7 above, the monomer solution without any surfactant was relatively Newtonian at 125 cps to 250 cps from 2 to 20 rpm, when measured with the Brookfield viscometer. The addition of octoxynol-7 as a surfactant resulted in a slight increase in viscosity, 250 cps to 375 cps at 2 to 20 rpm. The addition of octoxynol-9 as a surfactant produced a composition with a more pseudoplastic rheology (shear thinning), having a viscosity of 1000 cps at about 2 rpm and a viscosity of about 475 cps at about 20 rpm. The use of nonoxynol-7 and nonoxynol-9 as surfactants yielded significantly higher viscosity values than the octoxynol-9. They also demonstrated more pseudoplastic rheologies. The 2 and 20 rpm viscosities of the nonoxynol-7 and nonoxynol-9 were respectively, 4750, 1050, 6500 and 1400 cps. The nonoxynol-9 gave more viscosity per unit weight than the other surfactants tested.

EXAMPLES 15-18

Conditioning agents. Conductive compositions were prepared as per Examples 1-9 above, with variation of the conditioning agent added to the composition. All monomer solutions were prepared with those ingredients listed below in Table 8.

TABLE 8

| Solution | Wt % | Solution w/ silica Wt. Amt. (Example 15) | Solution w/ Kaolin Wt. Amt. (Example 16) | Solution w/ cellulose Wt. Amt. (Example 17) | Solution w/ carbon powder Wt. Amt. (Example 18) |
|---|---|---|---|---|---|
| 58% NaAMPS | 45.4 | 227.1 | 227.1 | 227.1 | 227.1 |
| Glycerol | 43.7 | 218.6 | 218.6 | 218.6 | 218.6 |
| Acrylic acid | 2.78 | 13.9 | 13.9 | 13.9 | 13.9 |
| 1% MBA in DI Water | 2.98 | 14.9 | 14.9 | 14.9 | 14.9 |
| 3% Irgacure | 0.50 | 2.5 | 2.5 | 2.5 | 2.5 |
| KCl | 1.99 | 9.9 | 9.9 | 9.9 | 9.9 |
| Silica | 2.49 | 12.4 | 0 | 0 | 0 |
| Kaolin | 0 | 0 | 12.4 | 0 | 0 |
| Cellulose | 0 | 0 | 0 | 12.4 | 0 |
| Carbon Powder | 0 | 0 | 0 | 0 | 12.4 |
| NaOH (50%) | 0.12 | 0.6 | 0.6 | 0.6 | 0.6 |
| Temp (° C.)/pH | | 24/3.44 | 24/3.48 | 24/3.52 | 23/3.47 |

The viscosity of the solutions was obtained as described above in Examples 1-9. The viscosity of each solution with the conditioning agent noted above in Examples 15-18 was determined, both before and after the addition of surfactant nonoxynol-9. The following solutions were compared: the monomer solution with nonoxynol-9 added as surfactant and silica as a conditioning agent, the monomer solution with nonoxynol-9 added as surfactant and kaolin instead of silica, the monomer solution with nonoxynol-9 added as surfactant and cellulose instead of silica, and the monomer solution with nonoxynol-9 added as surfactant and carbon powder instead of silica. The viscosity results are also set forth below in Table 9.

TABLE 9

| Viscosity | Example 15 | | Example 16 | | Example 17 | | Example 18 | |
|---|---|---|---|---|---|---|---|---|
| | Solution w/silica Wt. Amt. | Adding 0.5 g Non-oxynol-9 | Solution w/ Kaolin | Adding 0.5 g Non-oxynol-9 | Solution w/ cellulose | Adding 0.5 g Non-oxynol-9 | Solution w/ carbon powder | Adding 0.5 g Non-oxynol-9 |
| Viscosity at rpm 2 (cps) | 400 | 5200 | 200 | 200 | 200 | 200 | 200 | 200 |
| Viscosity at rpm 4 (cps) | 150 | 3200 | 100 | 100 | 100 | 100 | 100 | 100 |
| Viscosity at rpm 10 (cps) | 160 | 1740 | 120 | 120 | 80 | 100 | 100 | 100 |
| Viscosity at rpm 20 (cps) | 150 | 1130 | 110 | 110 | 90 | 100 | 100 | 100 |

It will be appreciated that various embodiments of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, or material.

What is claimed is:

1. A conductive composition comprising:
from about 15 weight % to about 50 weight % of a humectant or a mixture of humectants;
from about 18% to about 45% of a combination of monomers comprising, in polymerized form, from about 1 wt % to about 20 weight % of a first monomer, in which the first monomer comprises a mixture of an organic acid selected from the group consisting of acrylic acid, methacrylic acid, itaconic acid, trans-cinnamic acid, crotonic acid, linoleic acid, linolenic acid, maleic acid, sorbic acid, and combinations thereof, one or more salts thereof, and from about 15 weight % to about 45 weight % of a second monomer, in which the second monomer is one or more monomers of the formula $CH_2=CHC(O)XR$, in which X is O or NH and R is an unsubstituted or substituted alkyl group of from about 1 to about 5 carbon atoms;
from about 0.01 weight % to about 0.5 weight % of a surfactant selected from the group consisting of, nonylphenol ethoxylates, derivatives thereof, and combinations thereof, capable of providing the composition with a viscosity of from about 250 cps to about 40,000 cps; and
from about 0.05 weight % to about 7 weight % of a conditioning agent comprising silica.

2. The conductive composition according to claim 1, further comprising from about 0.1% to about 8% of an electrolyte or a mixture of electrolytes.

3. The conductive composition according to claim 1, further comprising a neutralizer selected from the group consisting of ammonium hydroxide, sodium hydroxide, potassium hydroxide, lithium hydroxide, and combinations thereof.

4. The conductive composition according to claim 1, further comprising a cross linking agent selected from the group consisting of bis-acrylamides, methacrylamides, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylates, and combinations thereof.

5. The conductive composition according to claim 1, further comprising a polymerization initiator selected from the group consisting of 2,2-azobisisobutyronitrile, 1hydroxycyclohexylphenyl ketone, 2-hydroxy-2-methyl-1-phenylpropan-1-one, 2-hydroxy-1-[4-(2-hydroxyethoxy)phenyl]-2-methyl-1-propan-1-one, 2,2-dimethoxy-2-phenylacetophenone, benzophenone, and combinations thereof.

6. The conductive composition according to claim 1, wherein the conductive composition has a pH of from about 2 to about 6.

7. The conductive composition according to claim 1, wherein the first monomer comprises a mixture of acrylic acid and sodium acrylate, and the second monomer comprises sodium 2-acrylamido-2-methylpropane sulfonate.

8. The conductive composition according to claim 3, wherein the humectant is selected from the group consisting of glycerol, sorbitol, and mixtures thereof, and the neutralizer comprises sodium hydroxide.

9. The conductive composition according to claim 1, wherein the nonylphenol ethoxylate is selected from the group consisting of nonoxynol-7 and nonoxynol-9.

10. The conductive composition according to claim 9, wherein the nonoxynol-7 provides the composition with an effective viscosity of from about 1500 cps to about 4800 cps.

11. The conductive composition according to claim 9, wherein the nonoxynol-9 provides the composition with an effective viscosity of from about 1200 cps to about 40,000 cps.

12. A biomedical electrode comprising:
a substrate; and
a layer of conductive composition on the substrate, the conductive composition comprising the conductive composition of claim 1.

13. A method for forming a conductive composition, comprising the steps of:
a) preparing a monomer reaction mixture comprising:
from about 15 weight % to about 50 weight % of a humectant or a mixture of humectants;
from about 18 weight % to about 45 weight % of a combination of monomers comprising from about 1 weight % to about 20 weight % of an organic acid selected from the group consisting of acrylic acid, methacrylic acid, itaconic acid, transcinnamic acid, crotonic acid, linoleic acid, linolenic acid, maleic acid, sorbic acid, one or more salts thereof, and combinations thereof, and from about 15 weight % to about 45 weight % of the sodium salt of 2-acrylamido-2-methylpropane sulfonic acid;
from about 0.01 weight % to about 0.5 weight % of a surfactant selected from the group consisting of nonylphenol ethoxylates, derivatives thereof, and combinations thereof;
from about 0.05 weight % to about 7 weight % of a conditioning agent comprising silica; and
(b) polymerizing the monomer or combination of monomers to form a copolymer as the conductive composition having a viscosity of from about 250 cps to about 40,000 cps.

14. The method according to claim 13, further comprising from about 0.1% to about 8% of an electrolyte or a mixture of electrolytes.

15. The method according to claim 13, further comprising a neutralizer selected from the group consisting of ammonium hydroxide, sodium hydroxide, potassium hydroxide, lithium hydroxide, and combinations thereof.

16. The method according to claim 13, further comprising a cross linking agent selected from the group consisting of bis-acrylamides, methacrylamides, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylates, and combinations thereof.

17. The method according to claim 13, further comprising a polymerization initiator selected from the group consisting of 2,2-azobisisobutyronitrile, 1hydroxycyclohexylphenyl ketone; 2-hydroxy-2-methyl-1-phenylpropan-1-one, 2-hydroxy-1-[4-(2-hydroxyethoxy)phenyl]-2-methyl-1-propan-1-one, 2,2-dimethoxy-2-phenylacetophenone, benzophenone, and combinations thereof.

18. The method according to claim 13, wherein the monomer reaction mixture comprises from about 20 weight % to about 30 weight % of the sodium salt of 2-acrylamido-2methylpropane sulfonic acid and about 5 weight % to 10 weight % of the acrylic acid.

19. The method according to claim 15, wherein the humectant comprises glycerol and the neutralizer comprises sodium hydroxide.

20. The method according to claim 13, wherein the nonylphenol ethoxylate is selected from the group consisting of nonoxynol-7 and nonoxynol-9, and wherein the conductive composition has a viscosity of from about 500 cps to about 40,000 cps.

21. The method according to claim 13, wherein the surfactant comprises nonoxynol-9, and the composition has an effective viscosity of from about 1200 cps to about 40,000 cps.

22. A conductive composition comprising:
from about 15 weight % to about 50 weight % of glycerol;
from about 18% to about 45% of a combination of monomers comprising, in polymerized form, from about 1 weight % to about 20 weight % of a first monomer comprising an organic acid selected from the group consisting of acrylic acid, methacrylic acid, itaconic acid, trans-cinnamic acid, crotonic acid, linoleic acid, linolenic acid, maleic acid, sorbic acid, one or more salts thereof, and combinations thereof, and from about 15 weight % to about 45 weight % of a second monomer, in which the second monomer is one or more monomers of the formula $CH_2=CHC(O)XR$, in which X is O or NH and R is an unsubstituted or substituted alkyl group of from about 1 to about 5 carbon atoms;
from about 0.01 weight % to about 0.5 weight % of nonoxynol-9; and
from about 0.05 weight % to about 7 weight % of silica, wherein the combination of nonoxynol-9 and silica provides the composition with a viscosity of from about 1200 cps to about 40,000 cps.

* * * * *